US00PP22093P2

(12) United States Plant Patent
Egger

(10) Patent No.: US PP22,093 P2
(45) Date of Patent: Aug. 23, 2011

(54) ***HEUCHERA* PLANT NAMED 'LIPSTICK'**

(50) Latin Name: ***Heuchera* spp.**
Varietal Denomination: Lipstick

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/800,260

(22) Filed: May 11, 2010

(51) Int. Cl.
*A01H 5/00* (2006.01)

(52) U.S. Cl. ..... Plt./440

(58) Field of Classification Search ..... Plt./440
See application file for complete search history.

*Primary Examiner* — June Hwu
(74) *Attorney, Agent, or Firm* — Klarquist Sparkman, LLP

(57) ABSTRACT

A new and distinct *Heuchera* plant substantially as shown and described, characterized by red flowers on repeat blooming spikes, medium small, bluish green leaves, a low mounding habit, and excellent vigor.

1 Drawing Sheet

Botanical denomination: *Heuchera* spp.
Variety designation: 'Lipstick'.

The present invention relates to a new and distinct cultivar of *Heuchera* and given the cultivar name of 'Lipstick'. *Heuchera* is in the family Saxifragaceae. *Heuchera* 'Lipstick' originated from a planned cross between *Heuchera* 542-1, a proprietary unreleased plant, as the seed parent, and *Heuchera* 465-1, a proprietary unreleased plant, as the pollen parent. Compared to the seed parent, *Heuchera* 542-1, the new cultivar has red rather than white flowers. Compared to the pollen parent, *Heuchera* 465-1, the new cultivar has flowers that are red rather than rose red.

Compared to *Heuchera* 'Blood Red' (U.S. Plant Pat. No. 17,153), the new cultivar is a larger plant, with larger leaves that are a bluer green when mature. The flowers of the new cultivar are smaller. The new cultivar is a repeat bloomer.

This new *Heuchera* is distinguished by:

1. red flowers on repeat blooming spikes,
2. medium small, bluish green leaves,
3. a low mounding habit,
4. and excellent vigor.

This new cultivar has been reproduced only by asexual propagation (cuttings and tissue culture). Each of the progeny exhibits identical characteristics to the original plant. Asexual propagation by stem cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The figure shows a two year old *Heuchera* 'Lipstick' in bloom, growing in the garden in full sun in May in Canby, Oreg.

DETAILED PLANT DESCRIPTION

The following is a detailed description of the new *Heuchera* cultivar based on observations of two-year-old specimens grown in the garden in full sun in May in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition.

Plant:

*Form.*—Basal rosette, herbaceous perennial.
*Hardiness.*—USDA Zone 4 to 9.
*Size.*—22 cm tall from top of the foliage to the ground and 36 cm wide.
*Habit.*—Low mound.
*Vigor.*—Excellent.
*Roots.*—Fibrous, freely branching, fine, and white in color; roots develop easily from cuttings.

Leaf:

*Type.*—Simple.
*Arrangement.*—Basal.
*Shape.*—Broadly ovate to orbicular.
*Lobing/division.*—5 main lobes, with 1 to 3 shallow secondary lobes.
*Venation.*—Palmate.
*Margins.*—Broadly crenate.
*Apex.*—Mucronulate.
*Base.*—Cordate, lobes overlapping at the base.
*Blade size.*—Grows to 7 cm long and 7 cm wide.
*Surface texture.*—Both sides glandular.
*Petiole description.*—Grows to 17 cm long and 2.5 mm wide, glandular hairs, Yellow Green 146D.
*Leaf color.*—New immature leaves topside, Green 138A with interveinal areas Yellow Green N144D, bottom side Green 138B; mature leaves topside, Green 135A along veins with a heavy silver veil closest to Greyed Green 189B, bottom side Yellow Green 147B.

Inflorescence:

*Size.*—Grows to 5.4 cm wide and 19 cm long.
*Type.*—Thyrse.
*Number of flowers per thyrse.*—85 per thyrse.
*Number of thyrse.*—About 40 in first spring bloom.
*Peduncle.*—Grows to 42 cm tall, 3 mm wide at base, Greyed Purple 187A.
*Pedicel.*—Variable in size, with glandular hairs, Greyed Purple 187A.

*Bloom period.*—May through June with sporadic rebloom all summer in Canby, Oreg.

Flower bud:

*Size.*—3 mm wide and 7 mm long.

*Description.*—Glandular puberulent, ovoid.

*Color.*—Red 53A with tip Greyed Purple 187A and base Red 47D.

Flower:

*Type.*—Perfect.

*Shape.*—Campanulate.

*Size.*—10 mm long and 11 mm wide.

*Petal description.*—5 in number, 3 mm long, 1 mm wide, spatulate with a clawed base, reflexed, tip acute, margin entire, glandular on top and bottom side, Red 53D on both sides.

*Calyx description.*—10 mm long and 11 mm wide, with 5 lobes, divided ⅔ way to the base, each 4 mm long and 3.5 mm wide, glandular hairs on both sides, tip obtuse, margin entire, inside Red 53A and outside Red 53A with tip and base Greyed Purple 187A.

*Stamen description.*—5 in number, 3 mm long, filament 2.5 mm long, White N155B, anthers Greyed Orange 164B, no pollen, male sterile.

*Pistil description.*—One central two beaked pistil, 4.4 mm long, ovary 2 mm long and 2 mm wide, Green Yellow 1D, style 2.5 mm long , White 155B.

*Fragrance.*—None.

*Lastingness.*—Each thyrse blooms for about 2 weeks on the plant.

Fruit:

*Type.*—Two beaked capsule.

*Size.*—7 mm deep by 2 mm wide.

*Fertility.*—Good.

*Color.*—Greyed Brown 199A.

Seed:

*Shape.*—Linear.

*Size.*—2 mm long.

*Color.*—Black, RHS 202A.

Disease and pest tolerance: No known resistance to rust, a common problem with light leaf type *Heuchera*. Excellent disease tolerance to powdery mildew. All *Heuchera* are susceptible to root weevils.

I claim:

1. A new and distinct *Heuchera* plant as herein illustrated and described.

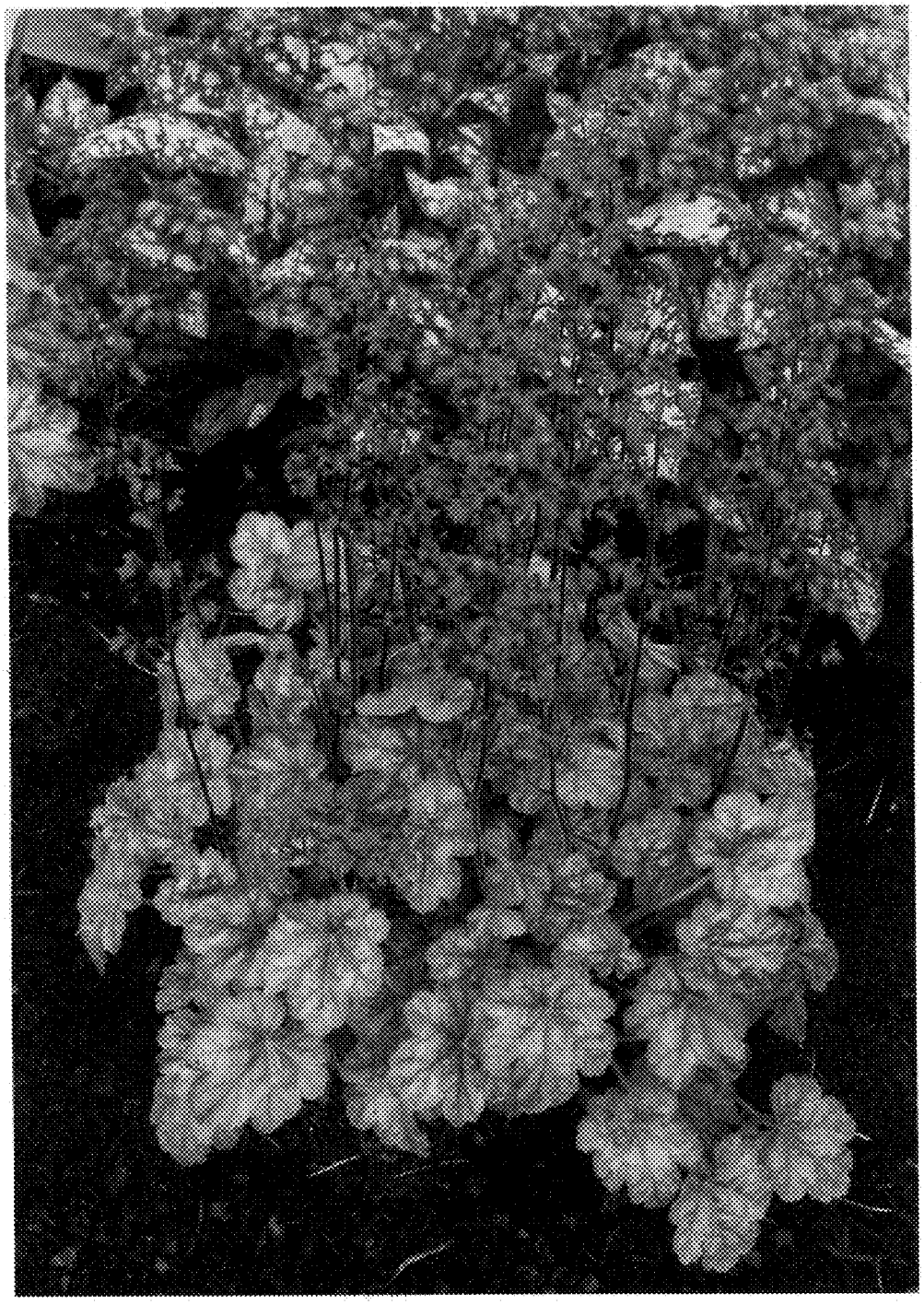

* * * * *